United States Patent [19]

Richwine

[11] Patent Number: 4,900,319
[45] Date of Patent: Feb. 13, 1990

[54] SANITARY NAPKIN

[76] Inventor: Mark H. Richwine, 7921 Stockwell St., Lincoln, Nebr. 68506

[21] Appl. No.: 250,509

[22] Filed: Sep. 29, 1988

[51] Int. Cl.[4] ............................................ A61F 13/16
[52] U.S. Cl. ................................. 604/385.1; 604/386; 604/387; 604/389
[58] Field of Search ...................... 604/385.1, 386, 387, 604/389, 397

[56] References Cited

U.S. PATENT DOCUMENTS

| | | | |
|---|---|---|---|
| 3,084,692 | 4/1963 | Atkinson | 604/385.1 |
| 3,115,877 | 1/1962 | Harwood | 604/385.1 X |
| 3,575,174 | 4/1971 | Mogor | 604/385.1 |
| 4,265,245 | 5/1981 | Glassman | 604/397 X |
| 4,285,343 | 8/1981 | McNair | 604/387 |
| 4,337,772 | 7/1982 | Roeder | 604/387 |
| 4,589,876 | 5/1986 | Van Tilburg | 604/385.1 |
| 4,681,577 | 7/1987 | Stern et al. | 604/382.1 X |

*Primary Examiner*—Richard J. Apley
*Assistant Examiner*—Rachel M. Healey
*Attorney, Agent, or Firm*—Zarley, McKee, Thomte, Voorhees & Sease

[57] ABSTRACT

A sanitary napkin includes an elongated forward portion, an elongated rearward portion, and an enlarged intermediate portion therebetween. The forward portion is longer than the rearward portion, and will extend forwardly beyond the vaginal area of the user. The enlarged intermediate portion will be located between the vaginal area and the anal area so as to absorb any discharge flowing along the body when in a reclined position. Adhesive strips on the sanitary napkin will allow the napkin to be removably fastened to the user's undergarments.

3 Claims, 1 Drawing Sheet

SANITARY NAPKIN

TECHNICAL FIELD

This invention relates generally to sanitary napkins, and more particularly to a sanitary napkin which is designed to improve absorbency characteristics when the user is in a reclined position.

BACKGROUND OF THE INVENTION

Sanitary napkins of current design are used to best advantage when the user is in either a standing or sitting position. Their effectiveness significantly decreases when the user is reclined in bed. In a reclined position, menstrual discharge will follow the body surface to the anal area since the conventional sanitary napkin has no portion which is designed to stop flow in this direction.

It is therefore a general object of the present invention to provide an improved sanitary napkin.

Another object of the present invention is to provide a sanitary napkin which will prevent the flow of discharge to the anal area.

Another object of the present invention is to provide a sanitary napkin which is effective when the user is in a reclined position.

These and other objects of the present invention will be apparent to those skilled in the art.

SUMMARY OF THE INVENTION

The sanitary napkin of the present invention includes an elongated forward portion, an elongated rearward portion, and an enlarged intermediate portion therebetween. The forward portion is longer than the rearward portion, and will extend forwardly beyond the vaginal area of the user. The enlarged intermediate portion will be located between the vaginal area and anal area so as to absorb any discharge flowing along the body when in a reclined position. The rearward portion will cover the lower buttock area. Adhesive strips on the sanitary napkin will allow the napkin to be removably fastened to the user's undergarments.

DESCRIPTION OF THE PREFERRED EMBODIMENT

Figure 1:
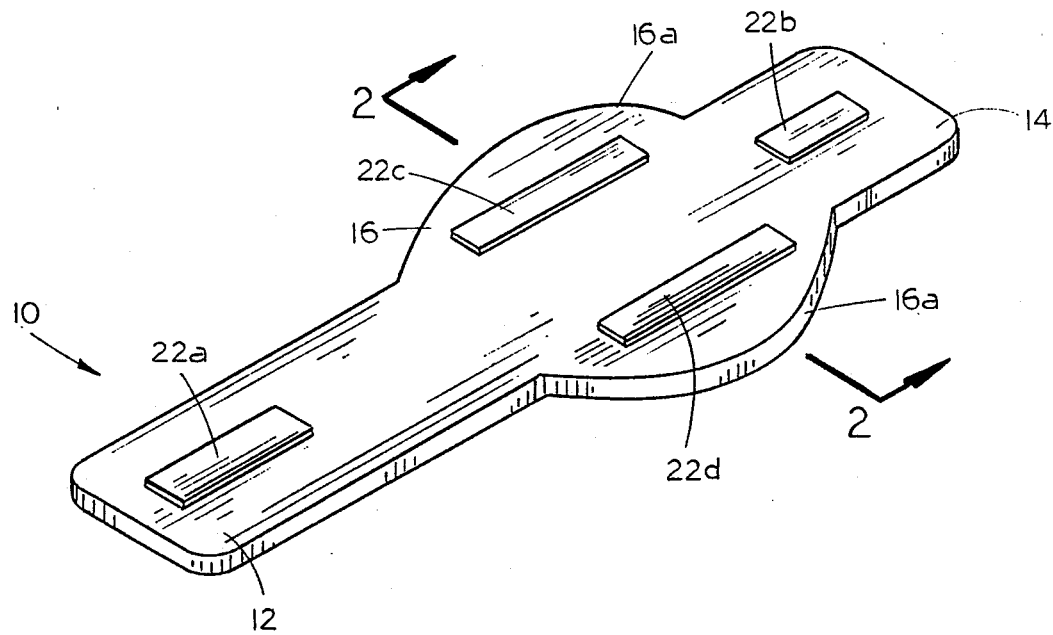
FIG. 1 is a perspective view of the invention.
Figure 2:
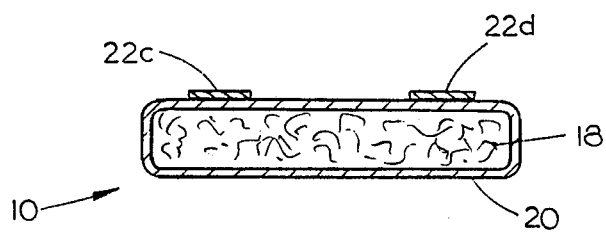
FIG. 2 is a sectional view taken at lines 2—2 in FIG. 1.

Referring now to the drawings, in which similar or corresponding parts are identified with the same reference numeral, and more particularly to FIG. 1, the sanitary napkin of this invention is designated generally at 10 and includes a forward portion 12, a rearward portion 14 and an intermediate portion 16.

Sanitary napkin 10 is composed of a soft, highly absorbent material 18, which is enclosed within a lining 20, as shown in the drawings. The overall length of sanitary napkin 10 is greater than that of sanitary napkins currently available and known. This additional length, in combination with the special intermediate portion 16, serves to provide additional absorbent material immediately forward of the anal area for use when the user is in a reclined position. It is has been found that a length of at least fifteen inches is necessary to achieve the results desired. Such a length is more than fifty percent larger than the standard nine to ten inch length of currently existing sanitary napkins.

As shown in the drawings, napkin 10 is generally elongated with forward elongated portion 12 longer than rearward elongated portion 14. Intermediate portion 16 is wider than forward and rearward portions 12 and 14, and has generally arcuate edges 16a such that the change in lateral dimension between the forward and rearward portions is gradual. Forward portion 12 is of a length which will extend forwardly of the vaginal area of the wearer. The enlarged intermediate portion 16 is located rearwardly of the vaginal area and slightly forward of the anal area in order to absorb any discharge which follows the body rearwardly. Rearward portion 14 covers the lower buttock area.

An elongated adhesive strip 22a is affixed longitudinally along forward portion 12, and may be attached to the undergarments of the wearer. A second adhesive strip 22b is located longitudinally on rearward portion 14 in a similar manner. A pair of parallel adhesive strips 22c and 22d are mounted to intermediate portion 16 and will fasten napkin 10 to the undergarments of the wearer.

Whereas the invention has been shown and described in connection with the preferred embodiment thereof, it will be understood that many modifications, substitutions and additions may be made which are within the intended broad scope of the appended claims. It can therefore be seen that the above-described invention fulfills at least all of the above-stated objectives.

I claim:

1. A sanitary napkin, comprising:
   an elongated napkin formed of a single, uniform-thickness layer of soft, absorbent material throughout the entire napkin;
   said napkin having a forward elongated portion, a rearward elongated portion and an intermediate portion;
   said forward and rearward portions being rectangular, non-tapering and equal in width;
   said forward portion having a length, measured longitudinally from said intermediate portion, greater than the length of the rearward portion, such that the forward portion will extend forwardly of a user's vaginal area and the rearward portion will extend over the lower buttock area of a user;
   said intermediate portion having a width greater than the width of said forward and rearward portions; and
   means on said napkin for removably mounting said napkin to an undergarment.

2. The sanitary napkin of claim 1, wherein said mounting means includes a first elongated adhesive strip mounted longitudinally on said forward portion, a second elongated adhesive strip mounted longitudinally on said rearward portion and third and fourth elongated adhesive strips mounted parallel and spaced apart on said intermediate portion.

3. The sanitary napkin of claim 1, wherein said forward, intermediate and rearward portions have opposing lateral edges, the intermediate portion having generally arcuate lateral edges formed between the lateral edges of the forward and rearward portions such that the width of the intermediate portion gradually increases from the width of the forward and rearward portions, the greatest width being located at the center of said intermediate portion.

* * * * *